US009629657B2

(12) United States Patent
O'Prey et al.

(10) Patent No.: US 9,629,657 B2
(45) Date of Patent: Apr. 25, 2017

(54) THORACIC ACCESS ASSEMBLY

(71) Applicant: Covidien LP, Mansfield, MA (US)

(72) Inventors: Cormac O'Prey, Bishops Stortford (GB); Valerie Anne Scott, Cambridge (GB); Rebecca Ann Wilkins, Saffron Walden (GB); Thomas John Hector Copeland, Cambridge (GB)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/596,396

(22) Filed: Jan. 14, 2015

(65) Prior Publication Data

US 2015/0126816 A1    May 7, 2015

Related U.S. Application Data

(62) Division of application No. 13/706,866, filed on Dec. 6, 2012, now Pat. No. 8,691,409.
(Continued)

(51) Int. Cl.
*A61B 17/34* (2006.01)
*A61B 17/02* (2006.01)
(Continued)

(52) U.S. Cl.
CPC ............ *A61B 17/3423* (2013.01); *A61B 1/32* (2013.01); *A61B 17/0218* (2013.01);
(Continued)

(58) Field of Classification Search
CPC ............ A61B 17/3423; A61B 17/0293; A61B 17/0218
(Continued)

(56) References Cited

U.S. PATENT DOCUMENTS 1,780,912 A    11/1930  Gau
1,810,466 A     6/1931  Deutsch
(Continued)

FOREIGN PATENT DOCUMENTS

DE       10001695 A1    2/2001
DE    102009014527 A1    9/2010
(Continued)

OTHER PUBLICATIONS

EP Search Report 11 25 0163 dated Jul. 6, 2011.
(Continued)

*Primary Examiner* — Christopher Beccia

(57) ABSTRACT

A surgical access assembly for accessing a cavity of a patient includes a proximal frame member, a distal frame member, and a membrane between the proximal and distal frame members. The proximal frame member is positionable adjacent an external surface of tissue and has first and second frame portions movable between a contracted condition and an expanded condition to expand an opening defined therethrough. The membrane defines a loop disposed about at least a portion of the proximal frame member at a proximal end thereof and is engaged to the distal frame member at a distal end thereof. The membrane is transitionable between a crumpled condition and an extended condition upon transitioning of the proximal frame member between the contracted condition and the expanded condition.

8 Claims, 11 Drawing Sheets

Related U.S. Application Data

(60) Provisional application No. 61/567,871, filed on Dec. 7, 2011.

(51) Int. Cl.
*A61B 1/32* (2006.01)
*A61B 17/00* (2006.01)

(52) U.S. Cl.
CPC ...... *A61B 17/0293* (2013.01); *A61B 17/3431* (2013.01); *A61B 17/3462* (2013.01); *A61B 2017/00902* (2013.01); *A61B 2017/0225* (2013.01); *A61B 2017/3427* (2013.01); *A61B 2017/3484* (2013.01); *A61B 2017/3492* (2013.01)

(58) Field of Classification Search
USPC .................................................. 600/201–246
See application file for complete search history.

(56) References Cited

U.S. PATENT DOCUMENTS

| | | |
|---|---|---|
| 2,313,164 A | 3/1943 | Nelson |
| 2,541,516 A | 2/1951 | Ivory et al. |
| 2,812,758 A | 11/1957 | Blumenschein |
| 3,782,370 A | 1/1974 | McDonald |
| 3,807,393 A | 4/1974 | McDonald |
| 3,965,890 A | 6/1976 | Gauthier |
| 4,130,113 A | 12/1978 | Graham |
| 4,263,899 A | 4/1981 | Burgin |
| 4,553,537 A | 11/1985 | Rosenberg |
| 5,007,900 A | 4/1991 | Picha et al. |
| 5,052,374 A | 10/1991 | Alvarez-Jacinto |
| 5,080,088 A | 1/1992 | LeVahn |
| 5,125,396 A | 6/1992 | Ray |
| 5,169,387 A | 12/1992 | Kronner |
| 5,231,974 A | 8/1993 | Giglio et al. |
| 5,232,451 A | 8/1993 | Freitas et al. |
| 5,269,754 A | 12/1993 | Rydell |
| 5,279,575 A | 1/1994 | Sugarbaker |
| 5,330,501 A | 7/1994 | Tovey et al. |
| 5,346,484 A | 9/1994 | Van Lindert |
| 5,391,156 A | 2/1995 | Hildwein et al. |
| 5,437,683 A | 8/1995 | Neumann et al. |
| 5,445,615 A | 8/1995 | Yoon |
| 5,460,170 A | 10/1995 | Hammerslag |
| 5,480,410 A | 1/1996 | Cuschieri et al. |
| 5,490,843 A | 2/1996 | Hildwein et al. |
| 5,503,617 A | 4/1996 | Jako |
| 5,520,610 A | 5/1996 | Giglio et al. |
| 5,524,644 A | 6/1996 | Crook |
| 5,556,385 A | 9/1996 | Andersen |
| 5,562,677 A | 10/1996 | Hildwein et al. |
| 5,653,705 A | 8/1997 | de la Torre et al. |
| 5,697,891 A | 12/1997 | Hori |
| 5,728,103 A | 3/1998 | Picha et al. |
| 5,755,660 A | 5/1998 | Tyagi |
| 5,755,661 A | 5/1998 | Schwartzman |
| 5,772,583 A | 6/1998 | Wright et al. |
| 5,776,110 A | 7/1998 | Guy et al. |
| 5,779,629 A | 7/1998 | Hohlen |
| 5,788,630 A | 8/1998 | Furnish |
| 5,803,921 A | 9/1998 | Bonadio |
| 5,810,721 A | 9/1998 | Mueller et al. |
| 5,846,193 A | 12/1998 | Wright |
| 5,875,782 A | 3/1999 | Ferrari et al. |
| 5,879,291 A | 3/1999 | Kolata et al. |
| 5,906,577 A | 5/1999 | Beane et al. |
| 5,908,382 A | 6/1999 | Koros et al. |
| 5,931,778 A | 8/1999 | Furnish |
| 5,935,107 A | 8/1999 | Taylor et al. |
| 5,944,736 A | 8/1999 | Taylor et al. |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | de la Torre et al. |
| 6,033,362 A * | 3/2000 | Cohn ............... A61B 17/02 600/210 |
| 6,033,425 A | 3/2000 | Looney et al. |
| 6,033,426 A | 3/2000 | Kaji |
| 6,036,641 A | 3/2000 | Taylor et al. |
| 6,048,309 A | 4/2000 | Flom et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 | 7/2001 | Fadem et al. |
| 6,254,534 B1 | 7/2001 | Butler et al. |
| 6,283,912 B1 | 9/2001 | Hu et al. |
| 6,309,349 B1 | 10/2001 | Bertolero et al. |
| 6,312,377 B1 | 11/2001 | Segermark et al. |
| 6,331,158 B1 | 12/2001 | Hu et al. |
| 6,332,468 B1 | 12/2001 | Benetti |
| 6,354,995 B1 | 3/2002 | Hoftman et al. |
| 6,361,492 B1 | 3/2002 | Santilli |
| 6,382,211 B1 | 5/2002 | Crook |
| 6,443,957 B1 | 9/2002 | Addis |
| 6,450,983 B1 | 9/2002 | Rambo |
| 6,458,079 B1 | 10/2002 | Cohn et al. |
| 6,500,116 B1 | 12/2002 | Knapp |
| 6,517,563 B1 | 2/2003 | Paolitto et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Segermark et al. |
| 6,746,467 B1 | 6/2004 | Taylor et al. |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,344,495 B2 | 3/2008 | Ravikumar et al. |
| 7,387,126 B2 | 6/2008 | Cox et al. |
| 7,393,322 B2 | 7/2008 | Wenchell |
| 7,473,222 B2 | 1/2009 | Dewey et al. |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |
| 7,594,888 B2 | 9/2009 | Raymond et al. |
| 7,650,887 B2 | 1/2010 | Nguyen et al. |
| 7,867,164 B2 * | 1/2011 | Butler ............... A61B 17/0293 600/208 |
| 8,961,409 B2 | 2/2015 | O'Prey et al. |
| 2001/0002429 A1 | 5/2001 | Hu et al. |

(56) References Cited

U.S. PATENT DOCUMENTS

| | | |
|---|---|---|
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0191371 A1 | 10/2003 | Smith et al. |
| 2004/0049099 A1 | 3/2004 | Ewers et al. |
| 2004/0054353 A1 | 3/2004 | Taylor |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0171405 A1* | 8/2005 | Rowland ............ A61B 17/0293 600/233 |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1 | 1/2006 | Douglas |
| 2006/0089537 A1 | 4/2006 | Schoellhorn |
| 2006/0106416 A1 | 5/2006 | Raymond et al. |
| 2006/0129165 A1 | 6/2006 | Edoga et al. |
| 2006/0149137 A1 | 7/2006 | Pingleton et al. |
| 2006/0149306 A1* | 7/2006 | Hart ................... A61B 17/3423 606/191 |
| 2006/0155170 A1 | 7/2006 | Hanson et al. |
| 2006/0247498 A1 | 11/2006 | Bonadio et al. |
| 2007/0027364 A1 | 2/2007 | Schwer |
| 2007/0073110 A1 | 3/2007 | Larson et al. |
| 2008/0132766 A1 | 6/2008 | Dant et al. |
| 2008/0234550 A1 | 9/2008 | Hawkes et al. |
| 2009/0118687 A1* | 5/2009 | Kristensen ............ A61F 5/448 604/342 |
| 2009/0204067 A1 | 8/2009 | Abu-Halawa |
| 2009/0265941 A1 | 10/2009 | Kurrus |
| 2009/0287060 A1* | 11/2009 | Pell ....................... A61B 17/02 600/201 |
| 2009/0299148 A1 | 12/2009 | White et al. |
| 2010/0210916 A1 | 8/2010 | Hu et al. |
| 2010/0234689 A1 | 9/2010 | Wagner et al. |
| 2011/0054260 A1* | 3/2011 | Albrecht ............ A61B 17/0218 600/208 |
| 2011/0144447 A1 | 6/2011 | Schleitweiler et al. |
| 2011/0201896 A1 | 8/2011 | O'Prey et al. |

FOREIGN PATENT DOCUMENTS

| | | |
|---|---|---|
| EP | 0177177 A2 | 4/1986 |
| EP | 2179699 A1 | 4/2010 |
| EP | 2228014 A1 | 9/2010 |
| EP | 2228024 A1 | 9/2010 |
| EP | 2238931 A1 | 10/2010 |
| EP | 2359759 A1 | 8/2011 |
| EP | 2417921 A1 | 2/2012 |
| EP | 2417922 A1 | 2/2012 |
| EP | 2462883 A1 | 6/2012 |
| EP | 2486882 A2 | 8/2012 |
| EP | 2524662 A2 | 11/2012 |
| GB | 2275420 A | 8/1994 |
| WO | 95/00197 A1 | 1/1995 |
| WO | 95/15715 A1 | 6/1995 |
| WO | 01/08563 A2 | 2/2001 |
| WO | 03/034908 A2 | 5/2003 |
| WO | 2004/075741 | 9/2004 |
| WO | 2005089655 A1 | 9/2005 |
| WO | 2010/136805 A1 | 12/2010 |
| WO | 2011/079374 A1 | 7/2011 |

OTHER PUBLICATIONS

EP Search Report 11 25 0164 dated Aug. 6, 2011.
EP Search Report 11 25 0719 dated Nov. 16, 2011.
EP Search Report 11 18 9987 dated Feb. 15, 2012.
EP Search Report 12160423.5 dated Jun. 25, 2012.
European Search Report EP 12180474 dated Nov. 20, 2012.
Partial European Search Report EP 12168483 dated Nov. 9, 2012.
European Search Report dated Nov. 15, 2013 in European Application No. 12195933.
European Office Action issued in corresponding application No. EP12195933.2 on Oct. 23, 2015.

* cited by examiner

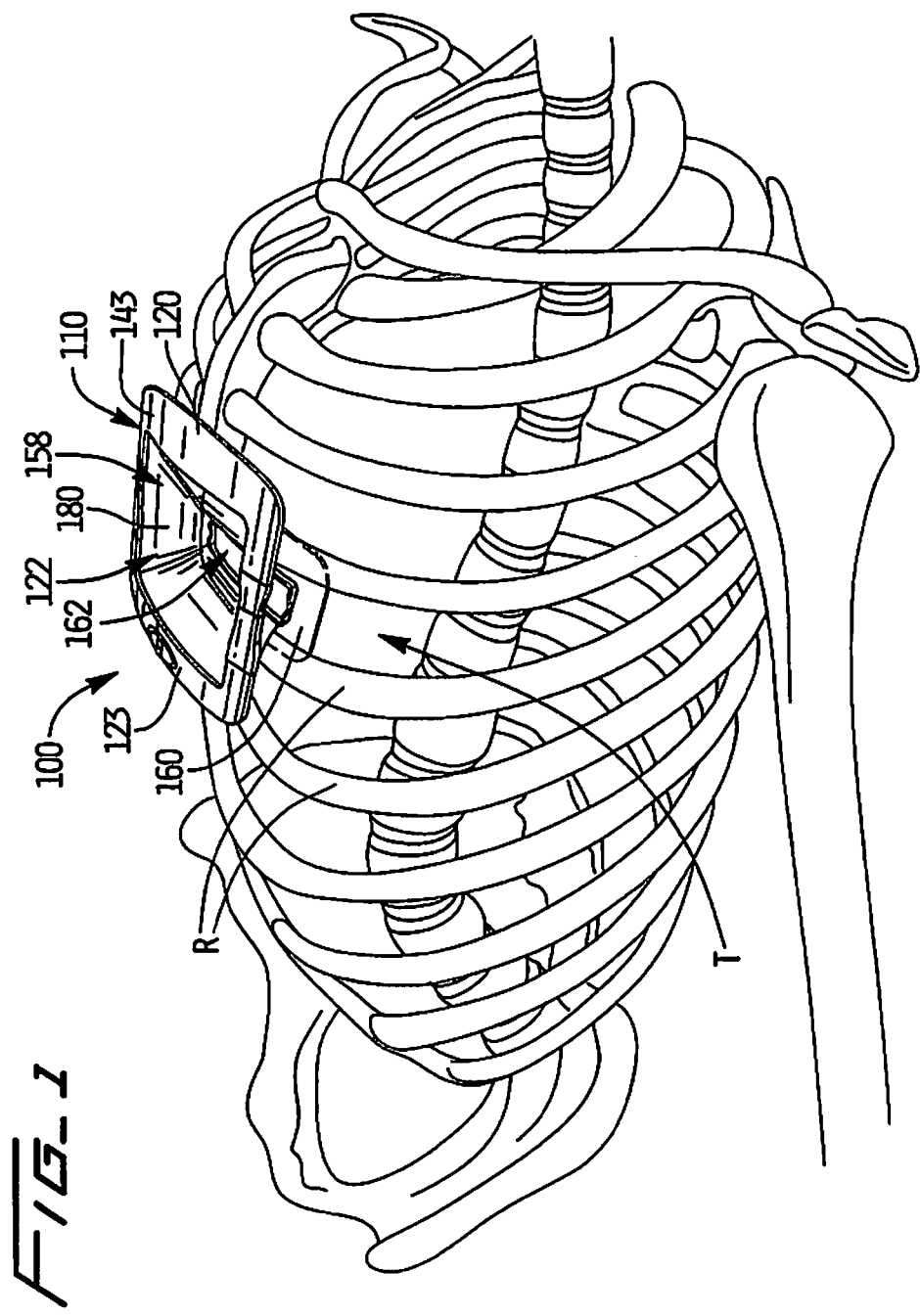
FIG_1

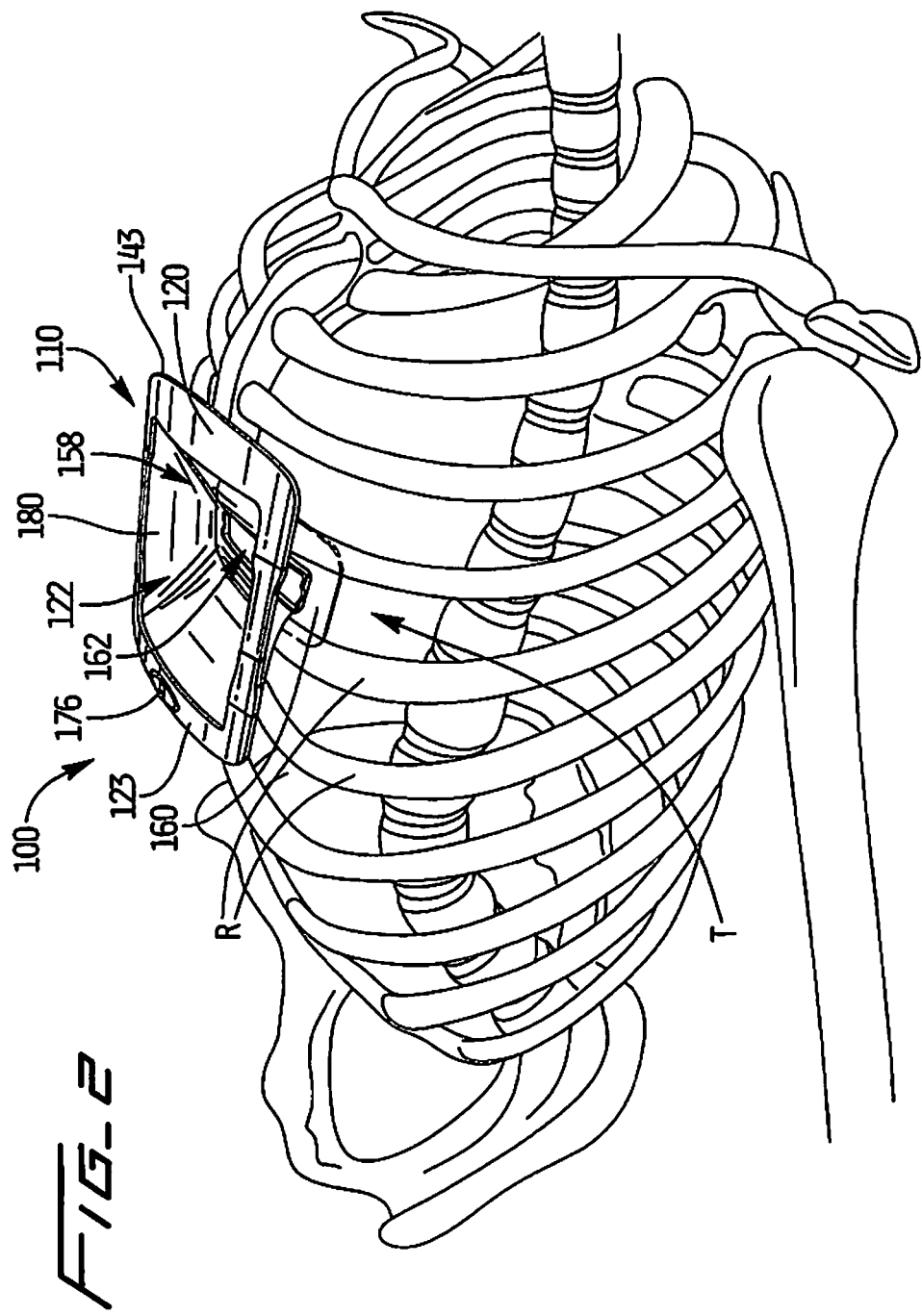

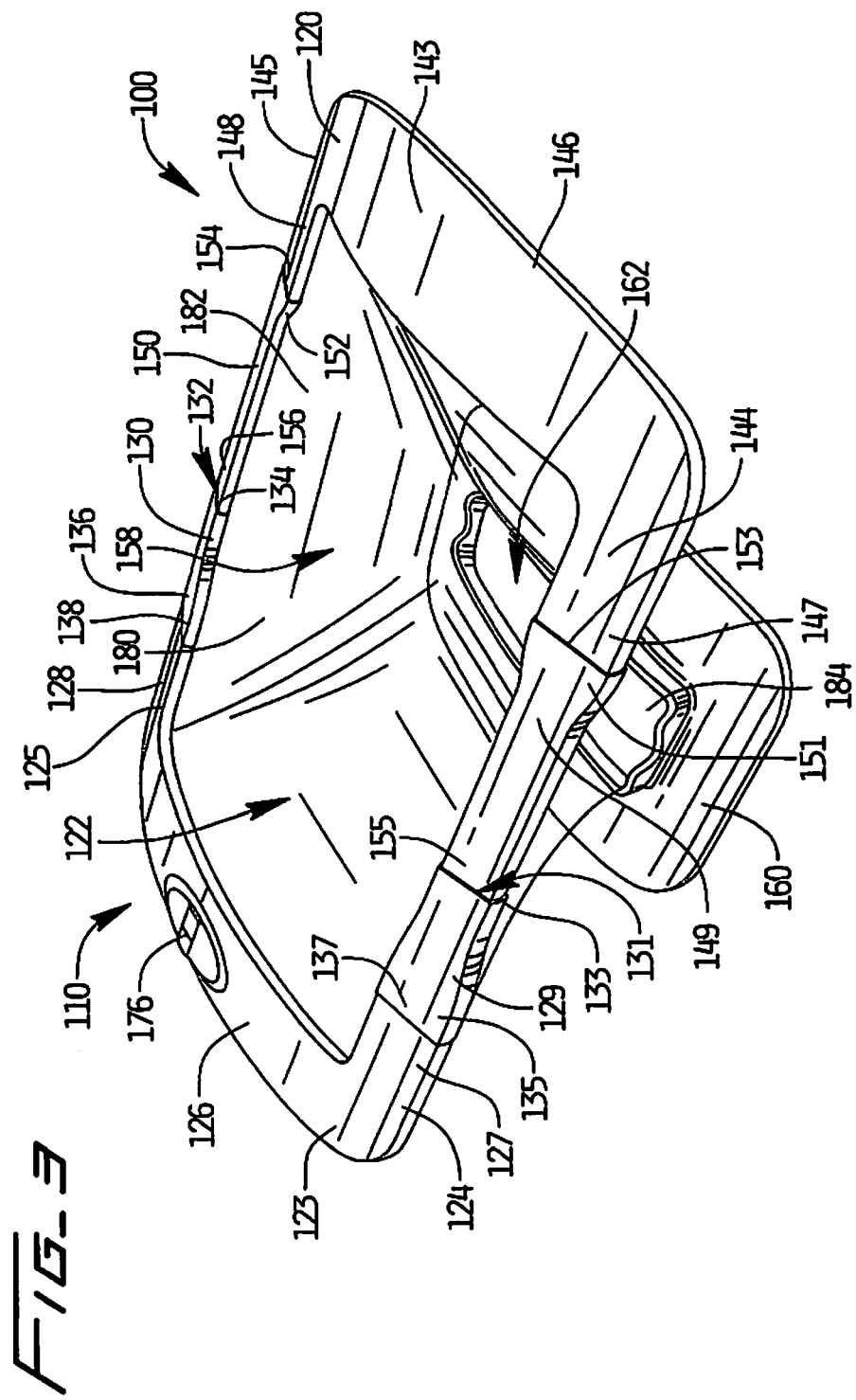

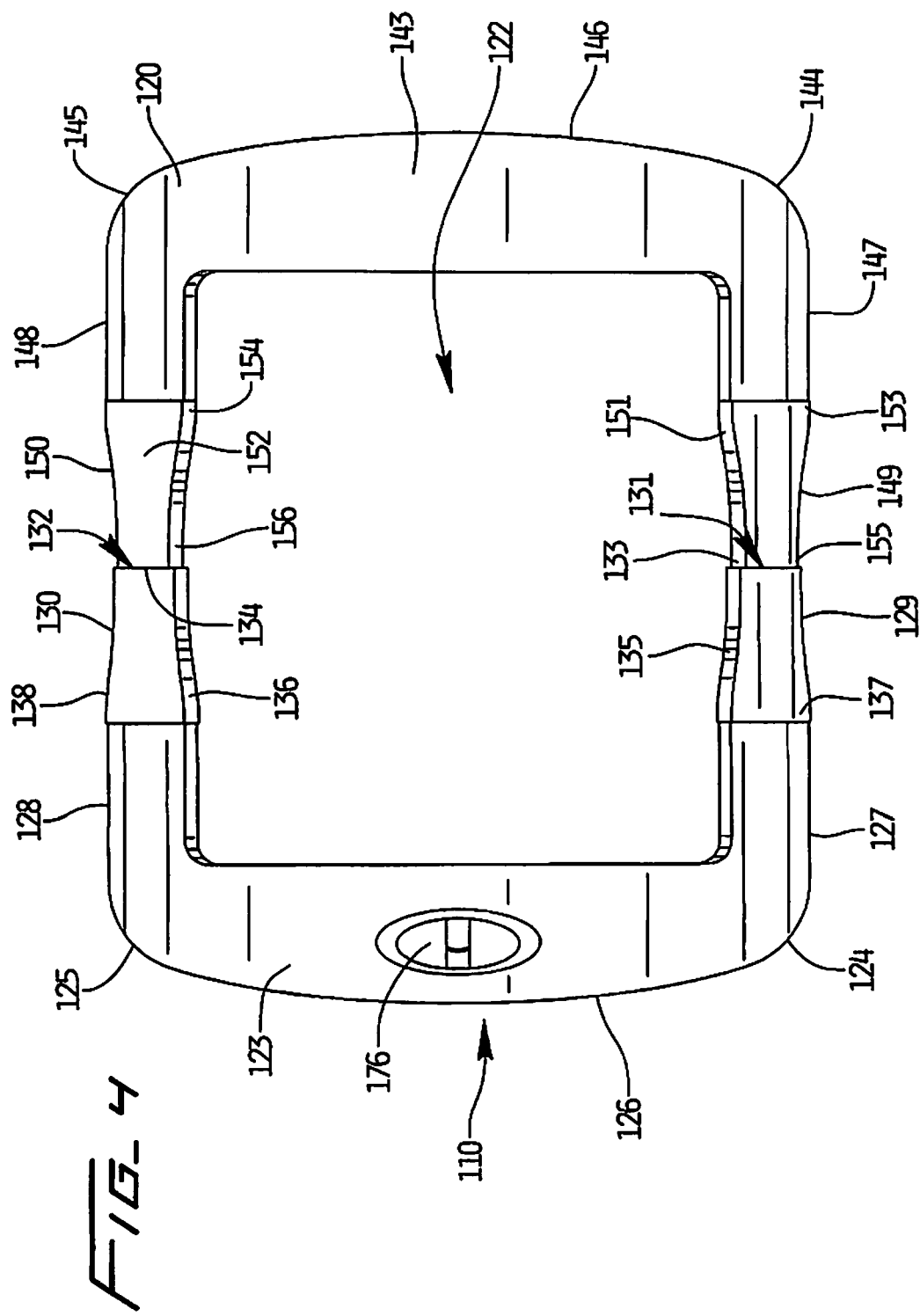

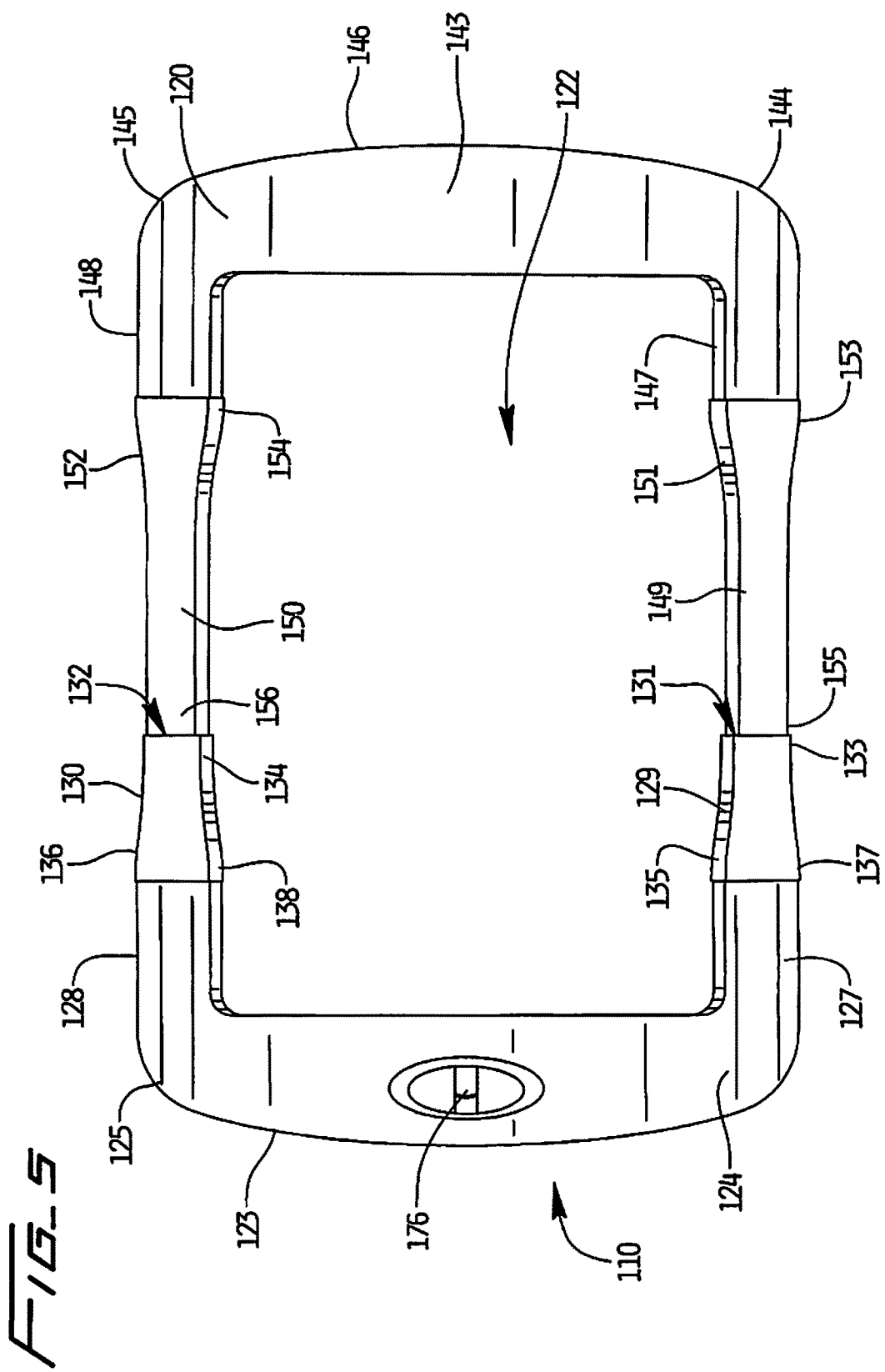

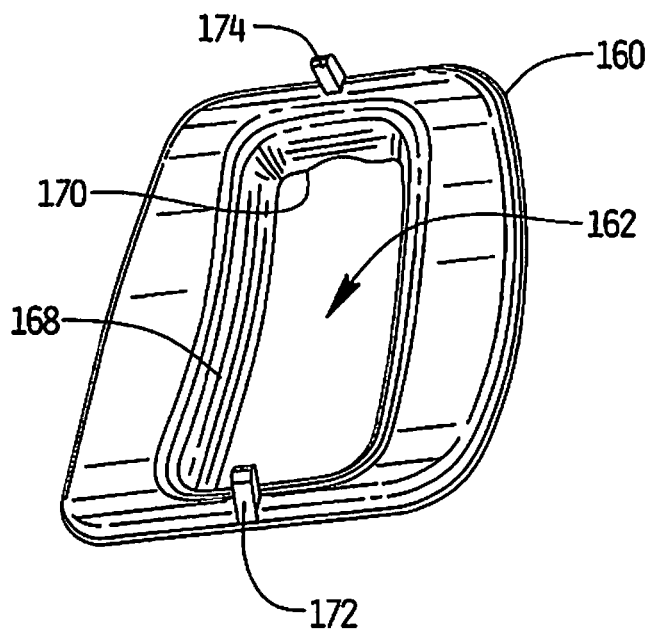
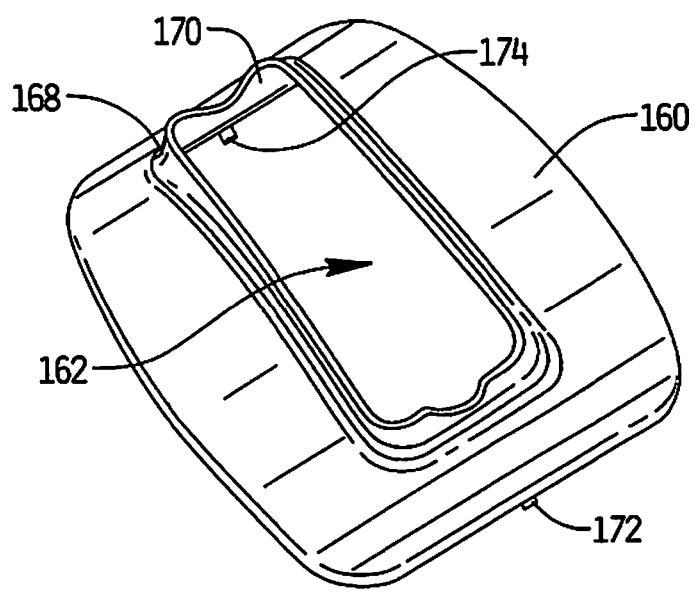

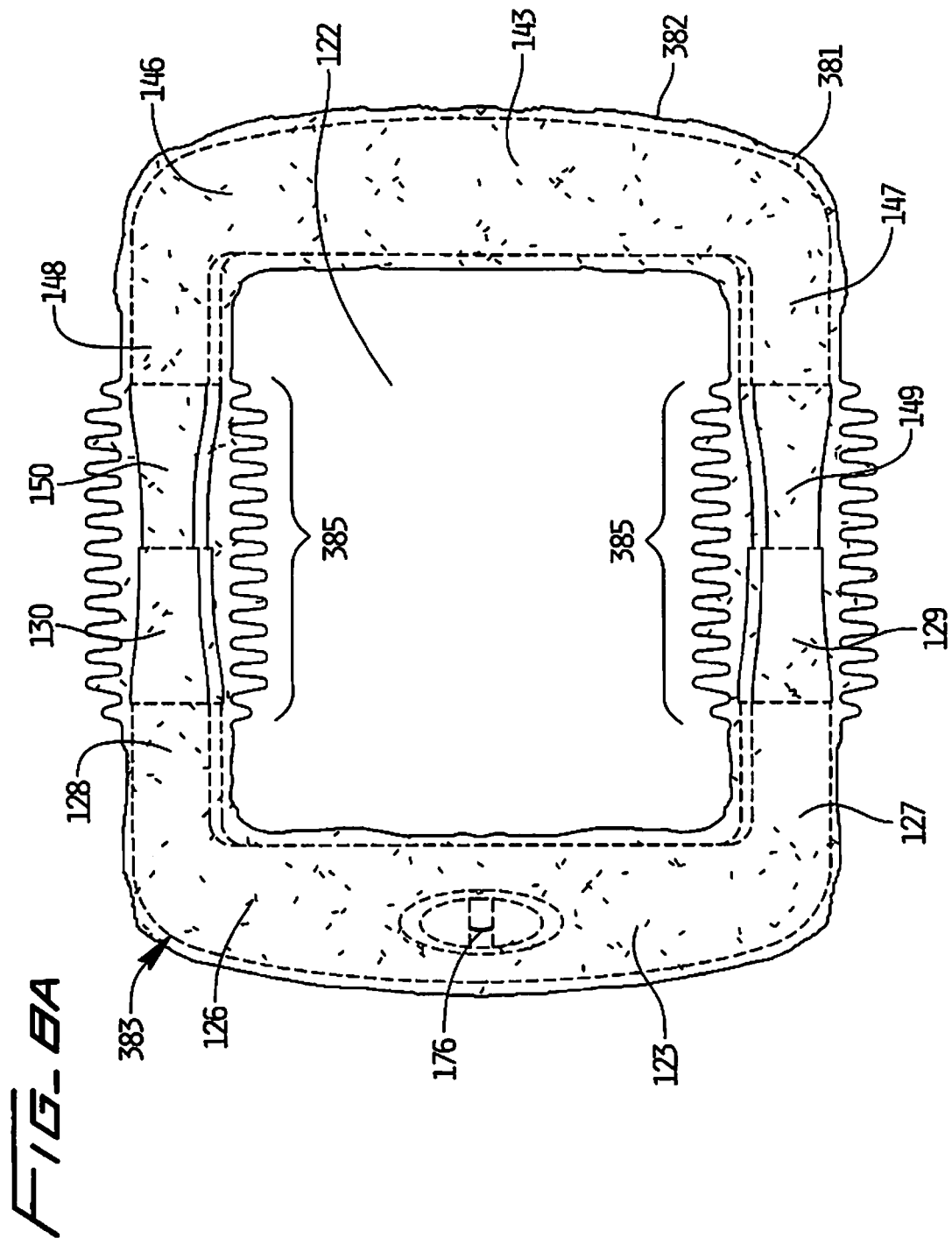

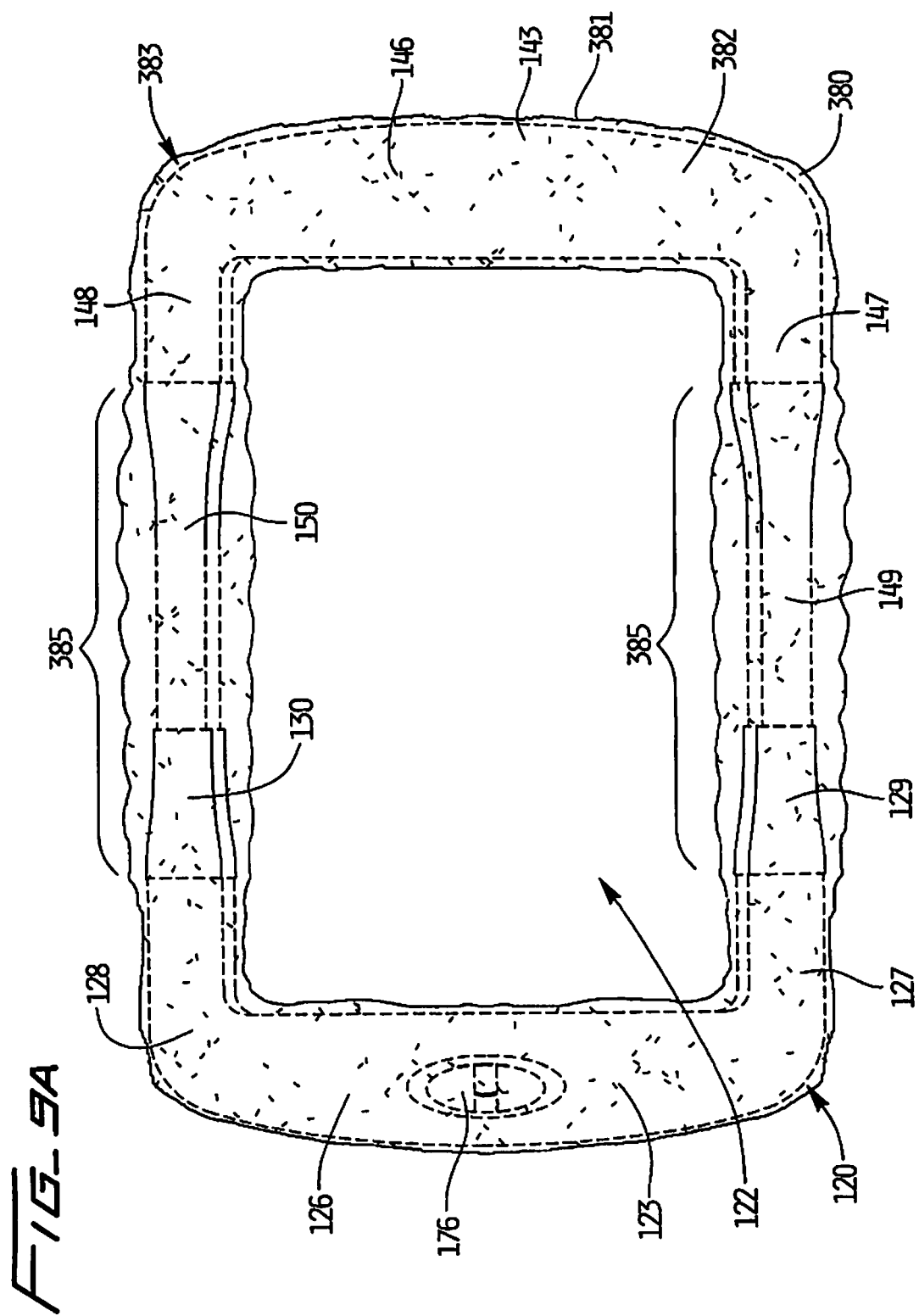

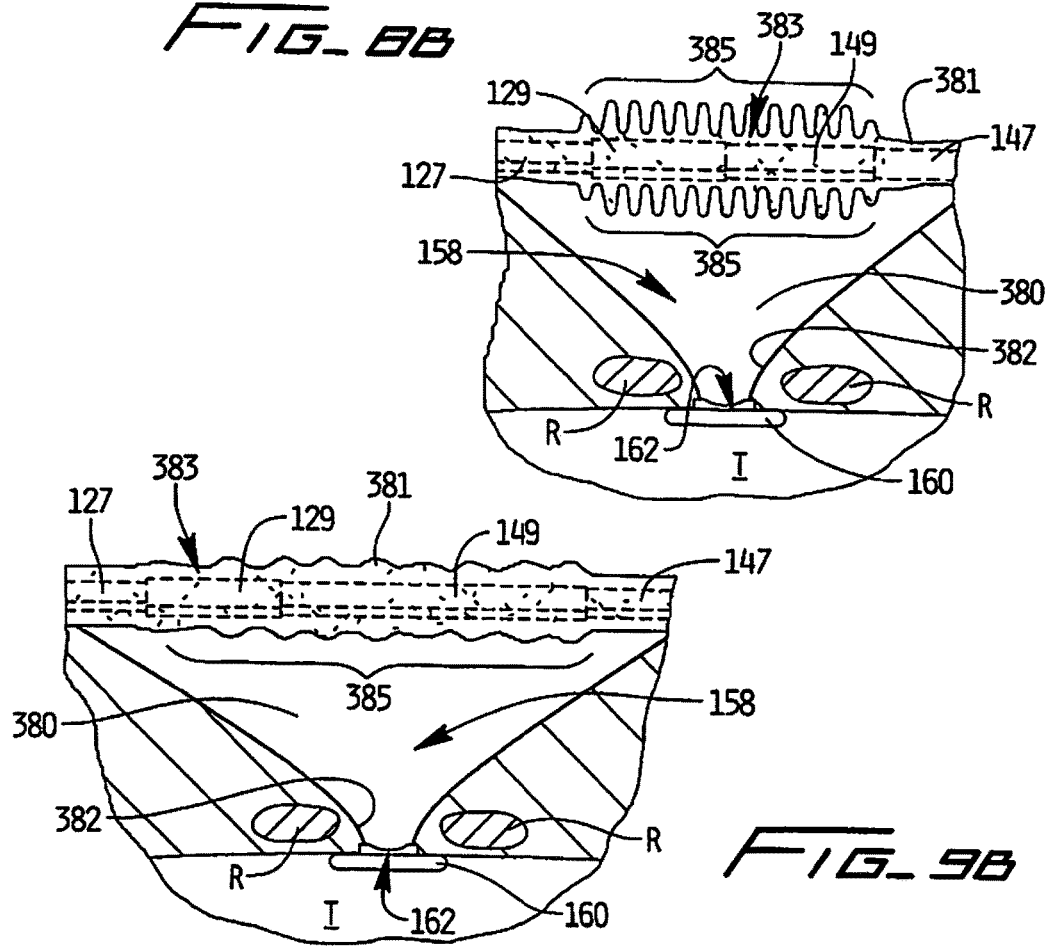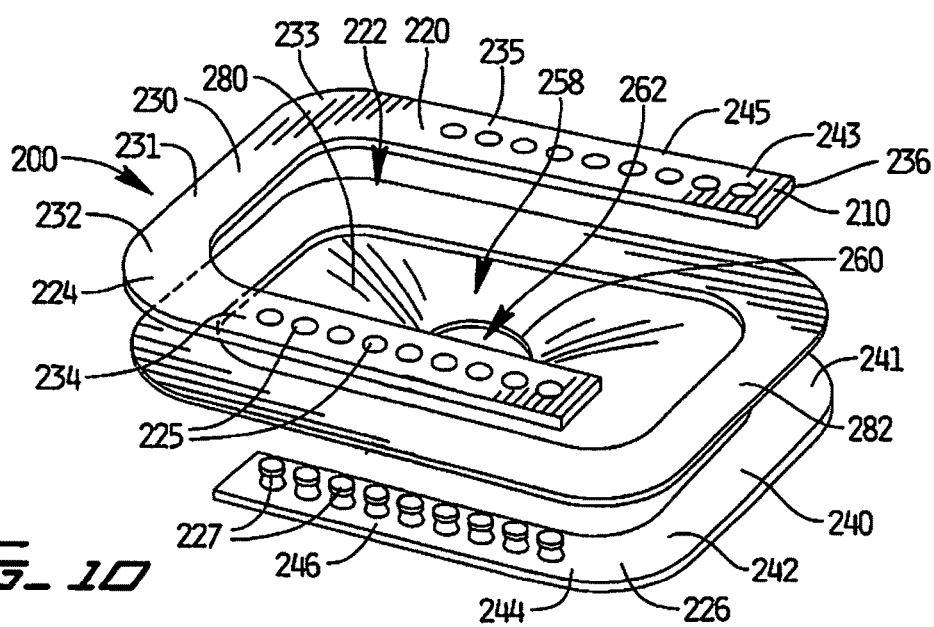

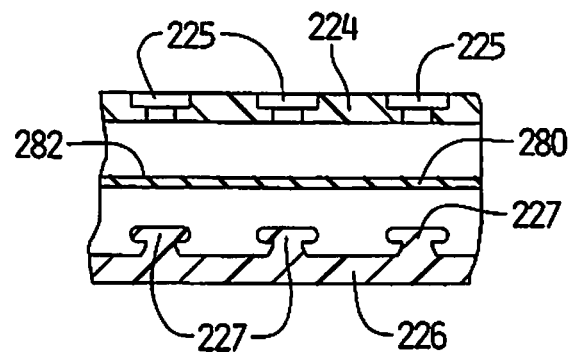
FIG_11
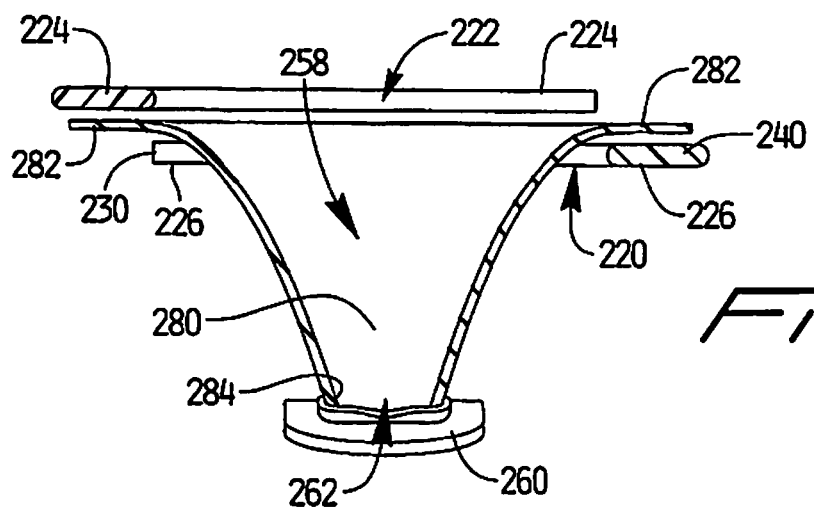
FIG_12
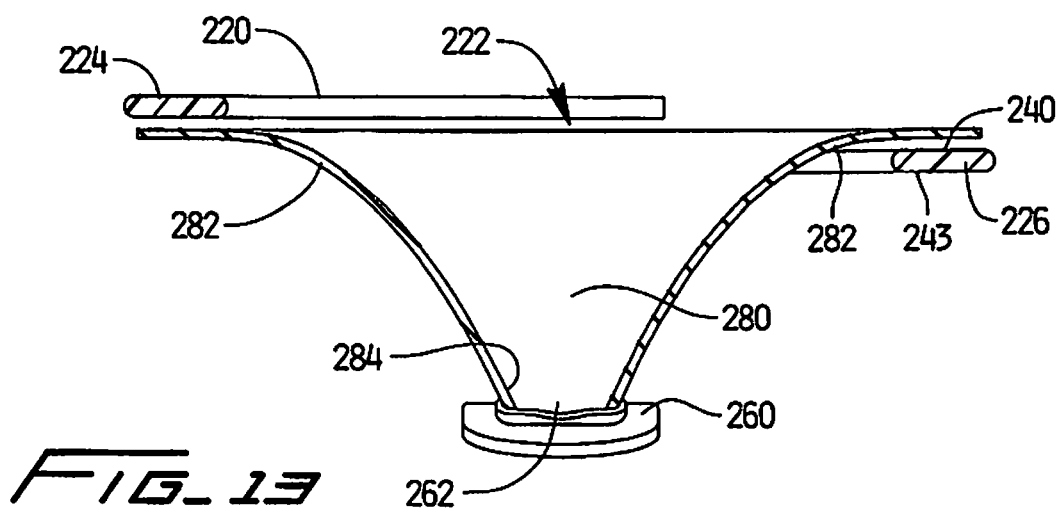
FIG_13

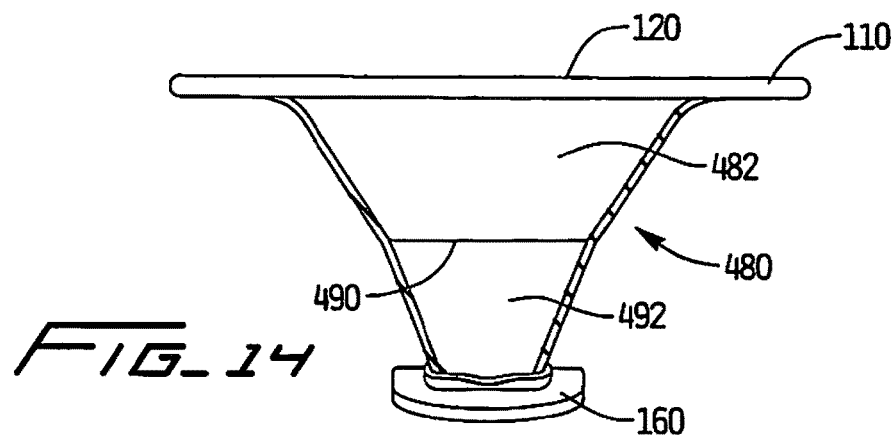
FIG_14
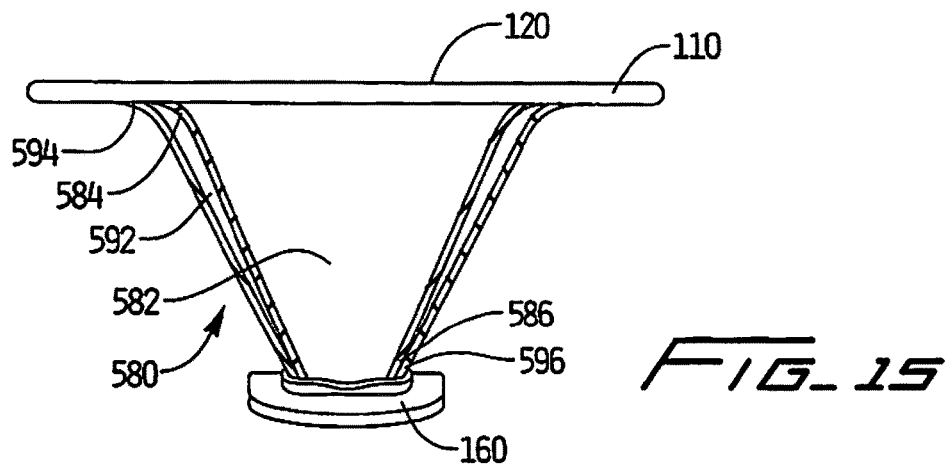
FIG_15
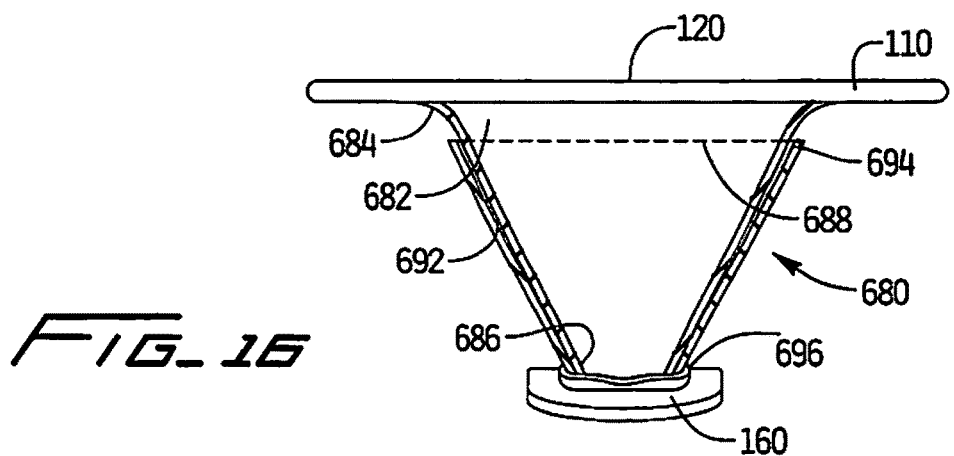
FIG_16

THORACIC ACCESS ASSEMBLY

CROSS-REFERENCE TO RELATED APPLICATIONS

This application is a divisional of U.S. patent application Ser. No. 13/706,866 filed Dec. 6, 2012, now U.S. Pat. No. 8,961,409, which claims benefit of U.S. Provisional Application No. 61/567,871 filed Dec. 7, 2011, and the disclosures of each of the above-identified applications are hereby incorporated by reference in their entirety.

BACKGROUND

1. Technical Field

The present disclosure relates generally to devices and techniques for performing surgical procedures. More particularly, the present disclosure relates to a surgical device for use during minimally invasive surgical procedures to facilitate access to an internal worksite with one or more surgical instruments, and/or the removal of tissue from the internal worksite.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity. Throughout the present disclosure, the term "minimally invasive" should be understood to encompass any and all such related procedures.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, an access device is placed within an opening in a patient's tissue, either pre-existing or created by a clinician, to define a passageway extending through which one or more of the above-mentioned surgical instruments are inserted. During minimally invasive thoracic procedures, for example, an access assembly is generally inserted into the space located between adjacent ribs of the patient, known as the intercostal space.

In the interests of facilitating visualization, the introduction of certain surgical instruments, and/or the removal of tissue specimens during minimally invasive thoracic procedures, it may be desirable to spread or retract the tissue adjacent the ribs defining the intercostal space. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for access devices which minimize post operative patient pain, while enabling the atraumatic retraction of tissue, maximizing access to the internal worksite, and facilitating the removal of tissue specimens therefrom.

SUMMARY

In accordance with one embodiment of the present disclosure, a surgical access assembly for accessing a cavity of a patient is provided. The access assembly generally includes a proximal frame member, a distal frame member, and a membrane. The proximal frame member is configured for positioning adjacent an external surface of tissue and defines a proximal opening therethrough. The proximal frame member includes first and second frame portions. One (or both) of the frame portions are moveable relative to one another between a contracted condition and an expanded condition. In the contracted condition, proximal opening defined through the proximal frame member defines a first length. In the expanded condition, the proximal opening defined through the proximal frame member defines a second length that is greater than the first length. The distal frame member is configured for insertion through an opening in tissue and positioning adjacent an internal surface of tissue. The distal frame member defines a distal opening extending therethrough. The membrane extends between the proximal and distal frame members. The membrane defines a loop that is disposed about a portion of (or the entire) the proximal frame member at a proximal end thereof and is engaged to the distal frame member at a distal end thereof. The membrane is transitionable between a crumpled or folded condition and an extended condition upon transitioning of the proximal frame member between the contracted condition and the expanded condition.

In one embodiment, the first frame portion of the proximal frame member includes a pair of sleeve portions extending from free ends thereof and the second frame portion of the proximal frame member includes a pair of extensions extending from free ends thereof. The extensions are slidably positionable within the sleeve portions to permit transitioning of the proximal frame member between the contracted condition and the expanded condition. Further, the extensions may be frictionally engaged within the sleeves.

In another embodiment, the sleeve portions and/or the extensions define tapered configurations such that the frictional engagement between the sleeves and the extension increases in strength as the proximal frame member is moved toward the expanded condition.

In another embodiment, the first frame portion and/or the second frame portion of the proximal frame member are manually manipulatable through the membrane between the contracted and expanded conditions.

In another aspect of the present disclosure, a surgical access assembly is provided including a proximal frame, a distal frame, and a membrane. The proximal frame member defines a proximal opening therethrough and is configured for positioning adjacent an external surface of tissue, while the distal frame member defines a distal opening therethrough and is configured for positioning adjacent and internal surface of tissue. The proximal frame member is selectively transitionable between a contracted condition and an expanded condition. Further, the proximal frame member includes an upper component and a lower component. The membrane extends between the proximal and distal frame members. The membrane is coupled to the distal frame member at a distal end thereof and includes a proximal end that is configured for positioning and securement between the upper and lower components of the proximal frame member upon engagement of the upper and lower components to one another.

In one embodiment, the upper and lower components of the proximal frame member are configured for snap-fit engagement with one another, although other configurations are contemplated. Further, the upper and lower components of the proximal frame member may be configured to releasably engage one another. In particular, one of the components may include a protrusion while the other component includes an aperture. The protrusion is configured for engagement with the aperture, with a portion of the membrane therebetween, to engage the upper and lower components to one another and secure the membrane therebetween.

In another embodiment, the proximal frame member includes a first frame portion and a second frame portion. Each of the first and second frame portions is formed from a portion of each of the upper and lower components of the proximal frame member. In such an embodiment, the first frame portion and/or the second frame portion may be movable relative to one another to permit transitioning of the proximal frame member between a contracted condition and an expanded condition.

In accordance with another aspect of the present disclosure, a surgical access assembly for accessing a cavity of a patient is provided comprising a proximal frame member configured for positioning adjacent an external surface of tissue and defining a proximal opening therethrough and selectively expandable from a contracted condition, wherein the proximal opening of the proximal frame member defines a first length, and an expanded condition, wherein the proximal opening of the proximal frame member defines a second length greater than the first length. A distal frame member is configured for positioning adjacent an internal surface of tissue, the distal frame member defining a distal opening therethrough. A membrane extends between the proximal frame member and the distal frame member, the membrane having a first portion and a second portion. The first portion is stiffer than the second portion.

In one embodiment, the first and second portions are configured as inner and outer layers of the membrane, respectively. Alternatively, the first and second portions may be configured as upper and lower portions of the membrane. The first and second portions may be formed from similar materials or different materials and/or may define different thicknesses. Additionally, one or both of the first and second portions may be coupled to both the proximal frame member and the distal frame member, or only one of the first and second portions may be coupled to both frame members.

BRIEF DESCRIPTION OF THE DRAWINGS

Various exemplary embodiments of the present disclosure are described herein below with reference to the drawings, wherein:

FIG. 1 is a side, perspective view illustrating a patient's skeletal structure with one embodiment of the presently disclosed surgical access assembly positioned within the intercostal space in a contracted condition;

FIG. 2 is a side, perspective view illustrating the patient's skeletal structure with the access assembly of FIG. 1 positioned within the intercostal space in an expanded condition;

FIG. 3 is a top, perspective view of the access assembly of FIG. 1 shown in the expanded position;

FIG. 4 is a top view of an upper member (frame) of the access assembly of FIG. 1 shown in the contracted position;

FIG. 5 is a top view of the upper member of the access assembly of FIG. 1 shown in the expanded condition;

FIG. 6 is a bottom, perspective view of a lower member (frame) of the access assembly of FIG. 1;

FIG. 7 is a top, perspective view of the lower member of the access assembly of FIG. 1;

FIG. 8A is a top view of the access assembly of FIG. 1, in the contracted condition with a membrane disposed about the proximal member thereof in a crumpled condition;

FIG. 8B is a side, cut-away view of the access assembly of FIG. 8A in the contracted position shown disposed within an opening in tissue between adjacent ribs of a patient;

FIG. 9A is a top view of the access assembly of FIG. 8A in the expanded condition with the membrane disposed about the proximal member thereof in an expanded condition;

FIG. 9B is a side, cut-away view of the access assembly of FIG. 8A in the expanded condition shown disposed within an opening in tissue between adjacent ribs of a patient;

FIG. 10 is a top, perspective view of another embodiment of an access assembly provided in accordance with the present disclosure and configured for positioning within the intercostal space;

FIG. 11 is a side, cross-sectional view of the proximal member of the access assembly of FIG. 10 showing the engagement between the components of the proximal member;

FIG. 12 is a side, cross-sectional view of the access assembly of FIG. 10 in the contracted condition with parts separated;

FIG. 13 is a side, cross-sectional view of the access assembly of FIG. 10 in the expanded condition with parts separated;

FIG. 14 is a side view of one embodiment of a membrane configured for use with any of the access assemblies of the present disclosure;

FIG. 15 is a side view of another embodiment of a membrane configured for use with any of the access assemblies of the present disclosure; and FIG. 16 is a side view of yet another embodiment of a membrane configured for use with any of the access assemblies of the present disclosure.

DETAILED DESCRIPTION OF THE EMBODIMENTS

Various embodiments of the presently disclosed access assembly, and methods of using the same, will now be described in detail with reference to the drawings wherein like references numerals identify similar or identical elements. In the drawings, and in the following description, the term "proximal" should be understood as referring to the end of the access assembly, or component thereof, that is closer to the clinician during proper use, while the term "distal" should be understood as referring to the end that is farther from the clinician, as is traditional and conventional in the art. Additionally, use of the term "tissue" herein below should be understood to encompass both the patient's ribs, and any surrounding tissues.

Turning now to FIGS. 1-3, one embodiment of the presently disclosed surgical access assembly, which is generally identified by reference numeral 100, is shown in use during the course of a minimally invasive thoracic surgical procedure. Access assembly 100 is depicted as a thoracic port that is configured and dimensioned for insertion into the intercostal space located between adjacent ribs "R" of a patient through an opening in tissue, such as an incision, in order to facilitate the insertion and manipulation of one or more surgical instruments (not shown) within the thoracic cavity "T." Although described in the context of a minimally invasive thoracic surgical procedure hereinbelow, it should be understood that surgical access assembly 100 may be configured and dimensioned for utilization during any minimally invasive surgical procedure wherein percutaneous access to an underlying internal worksite is desired, e.g., in laparoscopic or arthroscopic procedures.

With continued reference to FIGS. 1-3, access assembly 100 includes a frame 110 having a proximal or upper member (frame) 120 and a distal or lower member (frame) 160. Proximal member 120 and/or distal member 160 may be either rigid or flexible in structure, or may include both rigid components and flexible components. A flexible membrane 180 extends between and interconnects proximal and distal members 120, 160, respectively, of access assembly 100. More specifically, membrane 180 includes a proximal end 182 that is secured to proximal member 120, and a distal end 184 that is secured to distal member 160. Various components of access assembly 100 may be formed from any suitable biocompatible material, including, but not limited to, polymeric materials.

It is envisioned that membrane 180 (as well as the other embodiments of membranes disclosed herein, e.g., membranes 280-680 (FIGS. 8A-16), may be configured for soft tissue retraction. More particularly, it is envisioned that membrane 180 has a sufficient elasticity to permit retraction of a wide range of tissue thicknesses since there may be a wide range of tissue thicknesses among different patients. It is also envisioned that membrane 180 is of sufficient strength to resist accidental puncture by sharp surgical instrumentation, and to resist tearing. Additionally, it is envisioned that membrane 180 is made from a bio-compatible material to reduce the incidents of adverse reaction by a patient upon contact with the patient's tissue. The membrane 180 can also be made of a transparent material to allow the user to better view the surgical site and surrounding tissue.

As best shown in FIG. 3, proximal member 120 of frame 110 defines a proximal or upper access opening 122, while distal member 160 of frame 110 defines a distal, or lower access opening 162. In use, as will be described in greater detail below, proximal member 120 is configured to be positioned externally of the patient's body, e.g., adjacent an external surface of tissue, while distal member 160 is configured to be inserted through an opening in the patient's tissue and into position adjacent an internal surface of tissue in order to facilitate anchoring of access assembly 100 relative to the patient. As can be appreciated, proximal member 120, distal member 160, and membrane 180 cooperate to define a longitudinal passageway 158 extending between the respective proximal and distal openings 122, 162 of proximal and distal members 120, 160, respectively, of access assembly 100. Longitudinal passageway 158 is configured and dimensioned to removably receive one or more surgical instruments (not shown) therethrough to facilitate access to an internal surgical worksite, e.g., the thoracic cavity "T" (FIGS. 1 and 2). Further, as will be described in greater detail below, access assembly 100 is transitionable between a contracted condition (FIGS. 1 and 4), to facilitate insertion and removal of access assembly 100 from an opening in tissue, and an expanded condition (FIGS. 2 and 5), to facilitate anchoring of access assembly 100 within the opening in tissue.

Frame 110 of access assembly 100 may be formed from any structure (or structures) suitable for the intended purpose of facilitating the application and removal of a tensioning force to membrane 180, e.g., upon transitioning of access assembly 100 between the expanded and contracted conditions. Further, the respective proximal and distal members 120, 160 of frame 110 may define substantially rectangular configurations, as illustrated in FIGS. 1-7. However, other configurations of the respective proximal and distal members 120, 160 of frame 110 of access assembly 100, e.g., oval, other polygonal configuration, etc., are also contemplated.

As illustrated in FIGS. 4-5, proximal member 120 of frame 110 of access assembly 100 includes a first U-shaped member 123 and a second U-shaped member 143. First and second U-shaped members 123, 143, respectively, are mechanically coupled to one another in a manner facilitating relative movement therebetween, e.g., movement of first and second U-shaped members 123, 143, respectively, between the contracted condition (FIG. 4) and the expanded condition (FIG. 5), such that the dimensions of proximal opening 122 can be selectively increased and decreased to apply tension to or remove tension from membrane 180. More specifically, first and second U-shaped members 123, 143, respectively, are movable relative to one another between the contracted condition (FIGS. 1 and 4), wherein proximal opening 122 defines a relatively smaller dimension and wherein membrane 180 is substantially un-tensioned, thus facilitating the insertion and removal of access assembly 100 from the opening in tissue, and the expanded condition (FIGS. 2 and 5), wherein proximal opening 122 defines a relatively larger dimension and wherein membrane 180 is tensioned, thus facilitating the retraction of tissue and the anchoring of access assembly 100 within the opening in tissue.

With continued reference to FIGS. 4-5, first U-shaped member 123 includes a first end wall 126 and first and second side walls 127, 128, respectively. First side wall 127 extends from first end 124 of first end wall 126, while second side wall 128 extends from second end 125 of first end wall 126. Each side wall 127, 128 further includes a sleeve portion 129, 130. Each sleeve portion 129, 130, in turn, includes a lumen 131, 132, respectively, defined therein. More specifically, lumens 131, 132 extend through sleeve portions 129, 130, respectively, from the open free ends 133, 134 of respective sleeves 129, 130. Further, each sleeve portion 129, 130 includes a tapered portion 135, 136 that tapers from the fixed ends 137, 138 of tapered portions 135, 136 toward free ends 133, 134, respectively, thereof, such that lumens 131, 132 narrow in diameter from the fixed ends 137, 138 of tapered portions 125, 136 to the free ends 133, 134 of sleeve portion 129, 130, respectively.

Second U-shaped member 143, as best shown in FIGS. 4-5, likewise includes a second end wall 146 and third and fourth side walls 147, 148, respectively. Similarly as above, third side wall 147 extends from first end 144 of second end wall 146, while fourth side wall 148 extends from second end 145 of second end wall 146. Second U-shaped member 143 further includes a pair of extensions 149, 150 extending from third and fourth side walls 147, 148, respectively. Similar to sleeve portions 129, 130 of first U-shaped member 123, extensions 149, 150 define tapered portions 151, 152, respectively, that narrow in dimension from the fixed ends 153, 154 toward the free ends 155, 156, respectively, of extensions 149, 150.

Upon assembly of frame 110, tapered extensions 149, 150 of second U-shaped member 143 are inserted into sleeve portions 129, 130, respectively, of first U-shaped member 123. More specifically, sleeve portions 129, 130 of first U-shaped member 123 are configured to frictionally receive the respective extensions 149, 150 of second U-shaped member 143. Further, sleeve portions 129, 130 and/or extensions 149, 150 may be formed at least partially from a resiliently flexible material to increase the frictional retention of extensions 149, 150 within sleeve portions 129, 130 and/or may include surface features (not explicitly shown) configured to increase the frictional engagement between sleeves 129, 130 and extensions 149, 150. However, as can be appreciated, despite the frictional engagement between sleeve portions 129, 130 and extensions 149, 150, first and second U-shaped members 123, 143 are configured such that the clinician may still manipulate first and second U-shaped members 123, 143, respectively, toward, or apart from one another to a desired position, e.g., between the contracted condition and the expanded condition. In other words, the frictional engagement between sleeve portions 129, 130 and extensions 149, 150, respectively, is sufficiently strong to retain first and second U-shaped members 123, 143 in position relative to one another, but sufficiently weak to permit extension and/or contraction of frame 110 upon urging by the clinician. Further, by providing sleeve portions 129, 130 and extensions 149, 150 with tapered configurations, the frictional force retaining first and second U-shaped members 123, 143 in fixed relation relative to one another increases as extensions 149, 150 of second U-shaped member 143 are inserted further into sleeve portions 129, 130 of first U-shaped member 123, e.g., as U-shaped members 123, 143 are moved toward the contracted position. Such a configuration, as can be appreciated, inhibits inadvertent collapse of frame 110.

Additionally, as shown in FIGS. 4-5, a finger tab 176 may be provided on one or both of U-shaped members 123, 143, e.g., first U-shaped member 123, to facilitate manipulation of frame 110 between the contracted and expanded conditions. Alternatively, or additionally, the clinician may grasp end walls 126, 146 and pull them apart or push them together, in order to transition frame 110 between the contracted and expanded conditions.

It should be noted that, while the interconnections between first and second U-shaped members 123, 143, respectively, are described above as being frictional, it is envisioned that other suitable mechanisms for releasably securing first and second U-shaped members 123, 143, respectively, to one another may also be provided. Further, a lock, or locking mechanism (not shown) may also be provided to releasably lock U-shaped members 123, 143 in position relative to one another, e.g., to lock frame 110 in the contracted condition, the expanded condition, and/or any position therebetween. Such locking mechanism can include the slidable locking collar and engagement surfaces disclosed in U.S. Patent Application Pub. Nos. 2012/0041269, 2012/0143008, and 2012/0143009, the entire contents of each of which are incorporated herein by reference.

With reference now to FIGS. 6 and 7, distal member 160 of access assembly 100 will be described. Distal member 160 may be formed from a sufficiently flexible material to permit distal member 160 to be bent, reconfigured, or otherwise manipulated to facilitate insertion of distal member 160 through an opening in tissue and into the thoracic cavity "T" (FIGS. 1 and 2). As shown in FIGS. 6-7, distal member 160 is substantially rectangular in configuration, although other configurations are contemplated, and has a length defined along its longitudinal axis and a smaller width transverse to the longitudinal axis. Lower access opening 162, as mentioned above, is defined through distal member 160 and has a length defined along the longitudinal axis of distal member 160, e.g., along the length of distal member 160, that is greater than a width thereof, i.e., lower access opening 162 defines an elongated configuration for positioning between adjacent ribs "R" (FIGS. 1-2) of a patient.

A lip 168, extending toward proximal member 120, substantially surrounds lower access opening 162 about the periphery thereof. Lip 168 is configured to extend at least partially through the opening in tissue to protect the nerves adjacent the ribs "R" (FIGS. 1-2) once distal member 160 is inserted therethrough. Lip 168 may also be configured to protect other tissue structure(s) when used in other surgical applications.

Continuing with reference to FIGS. 6-7, a membrane mounting surface 170 is provided on a proximal surface of distal member 160 for mounting membrane 180 thereto via adhesives, hot gluing, welding, etc. Membrane 180 may alternatively be mounted to lip 168, to a distal surface of distal member 160, or in any other suitable configuration.

Referring momentarily to FIG. 3, membrane 180 may similarly be mounted to proximal member 120 of frame 110, e.g., via adhesives, hot gluing, welding, etc., or may otherwise be secured thereto in any suitable configuration.

Referring again to FIGS. 6-7, tabs 172, 174 may be provided on distal member 160 for receipt of sutures (not shown) or the surgeon's fingers or to provide grasping surfaces for surgical instrumentation (not shown) in order to facilitate removal of distal member 160 from an opening in tissue. That is, one or both of tabs 172, 174 can be grasped and pulled, thereby manipulating distal member 160 to facilitate removal through the opening in tissue.

Turning now to FIGS. 8A-9B, another embodiment of a membrane, flexible membrane 380, is shown configured for use with frame 110 of access assembly 100 or any other suitable access assembly that is moveable between a contracted condition and an expanded condition, e.g., access assembly 200 (see FIGS. 10-14). More specifically, membrane 380 includes a proximal loop portion 382 defined at a proximal end 381 thereof that is disposed about proximal member 120 of frame 110 to secure membrane 380 to proximal member 120. In other words, proximal member 120 is disposed within lumen 383 defined by proximal loop portion 382 of membrane 380 to secure membrane 380 thereto. The free end of membrane 380 may be folded over and adhered, or otherwise attached, to membrane 380 to define loop portion 382 having lumen 383 extending therethrough. Further, proximal loop portion 382 may be disposed completely about proximal member 120, as shown in FIGS. 8A-8B, or may only partially be disposed about proximal member 120, e.g., a portion of proximal member 120 may remain external of proximal loop portion 382 of membrane 380. Distal end 384 of membrane 380 may be secured to distal member 160 of frame 110 of access assembly 100 in any suitable fashion, e.g., via adhesives, hot gluing, welding, etc., as described above with regard to membrane 180.

With continued reference to FIGS. 8A-9B, proximal end 381 of membrane 380 defines a length that is at least equal to the perimeter of proximal member 120 of frame 110 when access assembly 100 is in the fully expanded condition (see FIGS. 9A-9B). In other words, proximal end 381 of membrane 380 defines a length, or diameter sufficient to fully cover proximal member 120 when frame 110 is fully expanded, such that membrane 380 does not interfere with the transitioning of proximal member 120 of frame 110 to the fully expanded condition. Proximal end 381 of membrane 380 is also configured to permit access assembly 100 to transition to the fully contracted condition (FIGS. 8A-8B). In other words, as shown in FIGS. 8A-8B, membrane 380 may defined a crumpled or pleated configuration along at least a portion thereof when access assembly 100 is disposed in the contracted condition. This configuration may be achieved simply due to the bunching up of the excess material of membrane 380 when proximal member 120 is disposed in the contracted condition, or, alternatively, membrane 380 may define an elastic portion 385 (or more elastic portion) that is biased toward this crumpled configuration.

As shown in FIGS. 9A-9B, when proximal member 120 of access assembly 100 is transitioned to the expanded condition, proximal end 381 of membrane 380 is fully extended, or tensioned about proximal member 120 of frame 110, such that there is no longer any, or such that there is very little, excess material at proximal end 381 of membrane 380. In other words, when access assembly 100 is moved to the expanded condition, membrane 380 is no longer crumpled up, but is tensioned, or extended to permit the extension of U-shaped members 123, 143 of proximal member 120 to the expanded condition. Further, in embodiments where membrane 380 includes an elastic portion 385, this elastic portion 385 may be stretched, or expanded from the initial, crumpled condition (FIGS. 8A-8B) to a tensioned, substantially linear condition (FIGS. 9A-9B) upon transitioning of access assembly 100 from the contracted condition to the expanded condition.

Referring additionally to FIGS. 1-7, proximal member 120 of frame 110 may be expanded by grasping U-shaped members 123, 143 through membrane 380 and pulling them apart from one another or, in embodiments where membrane 380 covers only a portion of U-shaped member 123, 143, the exposed portions of U-shaped members 123, 143 may be grasped and pulled apart from one other toward the expanded condition. Further, in embodiments where a locking mechanism (not shown) is provided, the locking mechanism (not shown) may be disposed within proximal loop portion 382, and, thus may be configured such that the clinician may manipulate the locking mechanism (not shown), e.g., between locked and unlocked states, through the membrane 380. As can be appreciated, slide-locks, release triggers, etc. may be provided for this purpose, as such mechanisms are relatively easily manipulatable, even through a membrane 380. Alternatively, the locking mechanism (not shown) may be disposed externally of proximal loop portion 382 of membrane 380.

Turning now to FIGS. 10-13, another embodiment of an access assembly provided in accordance with the present disclosure is generally identified by reference numeral 200. Access assembly 200, similar to access assembly 100, discussed above (see FIGS. 1-7), includes a frame 210 having a proximal member 220, a distal member 260, and a membrane 280 interconnecting proximal and distal members 220, 260, respectively. Proximal member 220 and/or distal member 260 may be either rigid or flexible in structure, or may include both rigid components and flexible components. Further, proximal member 220 and/or distal member 260 may be formed from any suitable biocompatible material (or materials), e.g., polymeric materials. Membrane 280 may be formed at least partially from a flexible material and includes a proximal end 282 configured for releasable engagement with proximal member 220, and a distal end 284 that is fixedly secured to distal member 260.

Similar to access assembly 100 (FIGS. 1-7), proximal member 220 of access assembly 200 defines a proximal access opening 222, while distal member 260 of access assembly 200 defines a distal access opening 262. Proximal member 220, distal member 260, and membrane 280 cooperate to define a longitudinal passageway 258 extending between the respective proximal and distal openings 222, 262 of proximal and distal members 220, 260, of access assembly 200. More specifically, proximal member 220 is configured for positioning adjacent an external surface of tissue, while distal member 260 is configured for positioning adjacent an internal surface of tissue, such that surgical instrumentation (not shown) may be inserted through longitudinal passageway 258 to facilitate access to an internal surgical worksite, e.g., the thoracic cavity "T." Further, access assembly 200, as will be described below, is transitionable between a contracted condition, for insertion and removal, and an expanded condition, for anchoring of access assembly 200 within an opening in tissue.

Proximal member 220 of access assembly 200 includes respective upper and lower components 224, 226 having similar configurations and dimensions although it is envisioned that upper and lower components 224, 226, respectively, may alternatively define different configurations. Each of the upper and lower components 224, 226, respectively, in turn, is separated into a pair of U-shaped portions, thus allowing proximal member 220 to be transitioned between the contracted condition and the expanded condition similarly as described above. More specifically, the first U-shaped portions of the respective upper and lower components 224, 226 of proximal member 220 cooperate to form first U-shaped member 230, which is moveable relative to second U-shaped member 240, formed from the second U-shaped portions of the respective upper and lower components 224, 226, such that the dimensions of proximal opening 222 may be selectively increased and decreased, thereby applying tension to or removing tension from membrane 280.

Proximal end 282 of membrane 280 is positioned between the respective upper and lower components 224, 226 of proximal member 220. Upper and lower components 224, 226, respectively, are releasably engageable with one another to secure proximal end 282 of membrane 280 therebetween. More specifically, as best shown in FIGS. 10 and 11, the respective upper and lower components 224, 226 of proximal member 220 include a plurality of apertures 225 and complementary protrusions 227, respectively, configured for releasably engaging one another to secure upper component 224 and lower component 226 to one another with proximal end 282 of membrane 280 therebetween. While apertures 225 and protrusions 227 are illustrated as being formed exclusively on upper component 224 and lower component 226, respectively, it is envisioned that each of the respective upper and lower components 224, 226 may include one or more apertures 225 and/or protrusions 227. Further, apertures 225 and protrusions 227 may be configured to frictionally engage one another, or may be configured to snap-fittingly engage one another. Additionally, proximal end 282 of membrane may extend between apertures 225 and protrusions 227 such that, upon engagement of apertures 225 and protrusions 227, a portion of membrane 280 is urged into each of apertures 225 by the corresponding protrusion 227 to secure membrane 280 therebetween, or may be displaced from apertures 225 and protrusions 227 such that membrane 280 is frictionally, or compressionally secured between upper and lower components 224, 226, respectively, e.g., sandwiched therebetween, upon engagement of apertures 225 and protrusions 227.

Alternatively, any other suitable releasable engagement mechanism may be provided for engaging upper and lower components 224, 226, respectively, to one another to secure proximal end 282 of membrane 280 therebetween. It is also envisioned that upper and lower components 224, 226, respectively, be fixedly secured to one another, e.g., via the use of an adhesive, to connect the respective upper and lower components 224, 226 of proximal member 220 to one another with membrane 280 therebetween. Further, it is also contemplated that upper and lower components 224, 226, respectively, be formed integrally, or monolithically with one another, similar to proximal member 120 of frame 110 of access assembly 100 (see FIGS. 1-7).

Proximal member 220, as mentioned above, is formed from upper and lower components 224, 226, respectively, and includes first U-shaped member 230 and a second U-shaped member 240. For simplicity of explanation, reference hereinbelow will be made to the different aspects of proximal member 220 as a whole, keeping in mind that upper and lower components 224, 226, when engaged to one another, cooperate to form proximal member 220. For example, although upper component 224 and lower component 226 each form a portion of each of the U-shaped members 230, 240 of proximal member 220, e.g., the upper and lower portions thereof, reference will only be made to the first and second U-shaped members 230, 240, respectively, as a whole.

With continued reference to FIGS. 10 and 11, in conjunction with FIG. 12, first U-shaped member 230 includes a first end wall 231 having first and second side walls 234, 235 extending from opposed ends 232, 233 thereof, while second U-shaped member 240 similarly includes a second end wall 241 having third and fourth side walls 244, 245, respectively, extending from opposed ends 242, 243 thereof. Each of the first and second side walls 234, 235, respectively, of first U-shaped member 230 defines a lumen 236 extending at least partially therethrough from the free end 238 thereof. Each of the lumens 236 of first and second side walls 234, 235, respectively, is configured to receive an extension 246 extending from third and fourth side walls 244, 245, respectively, of second U-shaped member 240. Lumens 236 may be formed by cooperating upper and lower channels (not explicitly shown) defined within the first U-shaped portions of upper and lower components 224, 226, respectively, of proximal member 220 upon engagement therebetween. Extensions 246, on the other hand, may be disposed on the second U-shaped portions of either (or both of) the upper component 224 or lower component 226 of proximal member 220. The interaction of lumens 236 and extensions 246 can provide an interference fit to retain these components in a select spread position.

The interconnections between first and second U-shaped members 230, 240, respectively, may be via frictional engagement (similar to that of access assembly 100, discussed above (see FIGS. 1-7)), or via any other suitable mechanism that permits selective movement of first and second U-shaped members 230, 240, respectively, relative to one another between a contracted condition and an expanded condition and that is capable of retaining first and second U-shaped members 230, 240, respectively, in a select spread (expanded) position.

Distal member 260 of access assembly 200, shown in FIGS. 10 and 13, may be configured similar to distal member 260 of access assembly 100, discussed above, and, thus, the description of distal member 260 of access assembly 200 will not be repeated here.

With reference now to FIGS. 14-16, several embodiments of membranes, e.g., membranes 480, 580, 680 configured for use with access assemblies 100, 200, or any other suitable access assembly, will be discussed. More specifically, although the following membranes 480, 580, 680 will be described with reference to frame 110 of access assembly 100, it is envisioned that these membranes 480, 580, 680 may be adapted for use with any other suitable access assembly frame, e.g., frame 210 of access assembly 200. Additionally, it is envisioned that any of the features of membranes 180-680 described herein, may similarly be applied to the other membranes 180-680.

Turning now to FIG. 14, membrane 480 is shown configured for use with frame 110 of access assembly 100. Membrane 480 includes a proximal portion 482 and a distal portion 492. Proximal portion 482 is engaged to proximal member 120 of frame 110 via any suitable mechanism, e.g., proximal portion 482 of membrane 280 may be snap-fit between components of proximal member 120, may include a loop disposed about proximal member 120, or may be adhered, or otherwise secured to proximal member 120 of frame 110. Distal portion 492 of membrane 480 is engaged to distal member 160 of frame 110 via any suitable mechanism, e.g., adhesion, hot gluing, welding, etc. Proximal portion 482 and distal portion 492 of membrane 480 are formed from separate materials and are engaged to one another at an intermediate position 490 of membrane 480. Proximal portion 482 and distal portion 492 of membrane 480 may be engaged to one another via any suitable mechanism, e.g., adhesion, stitching, gluing, welding, etc.

With continued reference to FIG. 14, proximal portion 482 of membrane is formed from a relatively elastic material, e.g., an elastomer, capable of expanding to permit transitioning of proximal member 120 from the contracted condition to the fully expanded condition and to retract tissue upon transitioning of access assembly 100 toward the expanded condition. Proximal portion 482 is also expandable in a vertical direction, allowing access assembly 100 to be used in a wide range of anatomical settings, e.g., for a wide range of tissue thicknesses, or depths. Distal portion 492, on the other hand, is formed from a relatively strong, more rigid material than proximal portion 482 that is configured to resist puncture, tearing, or other damage due to contact with surgical instrumentation (not shown) inserted through access assembly 100. Distal portion 492 also protects tissue surrounding the incision from similar damage from surgical instrumentation (not shown) and defines a more structured passageway through the opening in tissue to facilitate the insertion and removal of surgical instrumentation from the thoracic cavity "T" (FIGS. 1-2).

In some embodiments, proximal portion 482 of membrane 480 may be relatively thin, while distal portion 492 of membrane 480 may define a relatively thicker configuration. In such a configuration, proximal and distal portions 482, 492, respectively, may be formed from the same material, with the increased strength, toughness and/or rigidity of distal portion 492 attributed to the increased thickness of distal portion 492, or alternatively, proximal and distal portion 482, 492 may be formed from different materials that also have different thicknesses. Additionally, the dimensions of proximal and distal portions 482, 492, respectively, may be larger or smaller relative to one another, or may be substantially equal to one another, e.g., proximal portion 482 may define the majority of membrane 480, with distal portion 492 accounts for a relatively smaller portion of membrane 480. The reverse configuration may also be employed, or proximal and distal portions 482, 492 may define equal portions of membrane 480. Ultimately, the materials, configurations and/or dimensions of proximal and distal portions 482, 492, respectively, of membrane 480 may depend on the surgical procedure to be performed, the physical characteristics of the patient, and/or the anatomical location through which access assembly 100 is to be inserted.

Another embodiment of a membrane, membrane 580, configured for use with access assembly 100 (or any other suitable access assembly) is shown in FIG. 15. Membrane 580 includes an inner layer 582 and an outer layer 592 disposed about inner layer 582. Both the inner and outer layers 582, 592, respectively, are engaged to proximal member 120 of frame 110 of access assembly 100 at proximal ends 584, 594, respectively, thereof and to distal member 160 of frame 110 at distal ends 586, 596, respectively, thereof. More specifically, inner and outer layers 582, 592 of membrane 580 may be engaged to proximal member 120 at similar positions, as shown in FIG. 16, or may be engaged to proximal member 120 at different positions, e.g., inner layer 582 may be engaged to proximal member 120 along an inner periphery thereof, while outer layer 592 is engaged to proximal member 120 along an outer periphery thereof. Inner and outer layers 582, 592 may be engaged to proximal member 120 in any suitable fashion, such as those discussed above with respect to membranes 180-480. Further, membrane 580 may include a loop portion (not shown), similar to proximal loop portion 382 of membrane 380 (see FIGS. 8A-9B), that is disposed about proximal member 120 and interconnects inner and outer layers 582, 592, respectively, of membrane 580, thereby securing inner and outer layers 582, 592 to one another and to proximal member 120. Inner and outer layers 582, 592, respectively, of membrane 580 may be secured to distal member 160 of frame 110 in any suitable fashion, such as those discussed above with respect to membranes 180-480.

With continued reference to FIG. 15, inner and outer layers 582, 592, respectively, of membrane 580 may be formed from the same material, or may be formed from different materials, e.g., a relatively elastic and/or thin material for the inner layer to accommodate different tissue depths and a relatively rigid and/or thicker material for the outer layer to resist puncturing. In this embodiment of a thicker outer layer, the outer layer can in some embodiments be secured only to the distal member 160 and unattached to the proximal member 120 so as not to inhibit tensioning (flexing) of the inner layer to retract tissue. In embodiments of the same or different material, inner and outer layers 582, 592 form a double-layer configuration of membrane 580, thereby reducing the risk of puncturing or tearing completely through membrane 580, e.g., through both the inner and outer layers 582, 592, respectively, thereof.

Turning now to FIG. 16, membrane 680 is shown. Membrane 680, similar to membrane 580 (FIG. 16) is formed from inner and outer layers 682, 692, respectively. More specifically, inner layer 682 of membrane 680 is formed from a flexible, elastic material, e.g., a bio-compatible elastomer, and includes a proximal end 684 that is engaged to proximal member 120 of access assembly 100 in any suitable fashion and a distal end 686 that is engaged to distal member 160 of access assembly 100 in any suitable fashion. Inner layer 682 of membrane 680, as mentioned above, is formed from a flexible material that is capable of expanding to permit transitioning of proximal member 120 from the contracted condition to the fully expanded condition such that access assembly 100 may be used to retracted a wide range of tissue depths.

Continuing with reference to FIG. 16, outer layer 692 of membrane 680 is engaged to distal member 160 of frame 110 at a distal end 696 thereof and extends proximally therefrom toward proximal member 120 of frame 110. Outer layer 692 may also be engaged to proximal member 120 at a proximal end 694 thereof, may define a free proximal end 694, or, as shown in FIG. 16, may be engaged to an intermediate portion 688 of inner layer 682 at proximal end 694 of outer layer 692. Outer layer 692 may be engaged to inner layer 682 (or proximal member 120) in any suitable fashion, e.g., via adhesion, stitching, gluing, welding, etc. Alternatively, inner layer 682 of membrane 680 may be looped about proximal member 120 of frame 110, similar to membrane 380 (see FIGS. 8A-9B), with outer layer 692 secured to the portion of inner layer 682 disposed about proximal member 120. Further, in some embodiments where outer layer 692 defines a free proximal end 694 (or in any other configuration of membrane 680), it is envisioned that outer layer 692 can define a sufficient length to extend proximally from distal member 160 completely through the opening in tissue.

With continued reference to FIG. 16, outer layer 692 may be formed from a relatively tough and/or thick material to resist puncture, tearing, or other damage to membrane 680, while also protecting tissue surrounding the opening therein. Further, although outer layer 692 is somewhat flexible to conform to the dimensions of the incision and surrounding tissue, it is envisioned that outer layer 692 is sufficiently rigid to retain its shape in the absence of substantial forces acting thereupon. In other words, outer layer 692 is configured to substantially retain its funnel-shaped configuration during insertion and manipulation of access assembly 100 through an incision in tissue. However, it is also envisioned that outer layer 692 is also sufficiently flexible to permit full movement of proximal member 120 between the contracted and expanded conditions.

The use and operation of the presently disclosed thoracic access assemblies, e.g., access assemblies 100, 200 and membranes 180-680 for use therewith, will now be described. The following description will be made with reference to access assembly 100 and membrane 180, shown in FIGS. 1-7. The use and operation of access assembly 200 and/or membranes 280-680 in combination with any of the access assemblies discussed herein is substantially similar to that of access assembly 100 and membrane 180 and, thus, will not be repeated for purposes of brevity.

Initially, an incision, or opening (not explicitly shown) is made through the body tissue of a patient between adjacent ribs "R" of the patient. Thereafter, distal member 160 of thoracic access assembly 100 is compressed or reconfigured, e.g. bent, using appropriate surgical instrumentation or by the clinician's hands, and is inserted through the opening, i.e., between adjacent ribs "R" of the patient. Once positioned within the thoracic cavity "T," distal member 160 is released, allowing distal member 160 to return to its original condition. Distal member 160 may then be maneuvered to abut the internal surface of tissue underlying the adjacent ribs "R" of the patient. This may be facilitated by grasping proximal member 120 and pulling proximal member 120 in an upward direction. It should be noted that in this initial position, proximal member 120 is in the contracted condition (see FIGS. 1 and 4) and remains disposed externally of the incision. Further, as can be appreciated, with distal member 160 positioned adjacent to the internal surface of tissue, and with proximal member 120 positioned on an external side of tissue, flexible membrane 180 extends through the opening, thereby protecting the opening from contamination. It should also be appreciated that, once access assembly 100 is positioned within the opening in tissue, the longitudinal axis of distal member 160 is positioned substantially along the length of the opening, e.g., along and between the ribs "R," to facilitate retraction of the tissue adjacent the opening. That is, in this manner, longitudinal passageway 158 through access assembly 100 tracks the opening shape and therefore accommodates the insertion and removal of surgical instrumentation from the thoracic cavity "T" with minimal trauma to the patient.

Once distal member 160 has been positioned within the opening, as described above, proximal member 120 of frame 110 may be moved from the contracted condition to the expanded position for anchoring access assembly 100 between adjacent ribs "R" of the patient (see FIGS. 2 and 9B). More particularly, in order to transition proximal member 120 of frame 110 from the contracted position to the expanded condition, as best shown in FIGS. 1-2 and 4-5, the clinician may grasp first and/or second end walls 126, 146 of first and second U-shaped members 123, 143, respectively, and pull them apart from each other against the frictional bias maintaining first and second U-shaped members 123, 143 in fixed relation relative to one another. Alternatively, in embodiments where a locking mechanism is provided, the access assembly is expanded to a desired position then locked in that position.

As can be appreciated, as first and second U-shaped members 123, 143, respectively, are moved from the contracted condition toward the expanded condition, proximal access opening 122 is expanded, and membrane 180 is increasingly tensioned. As such, first and second U-shaped members 123, 143 of proximal member 120 may be moved to a desired position to impart a desired tensioning force on membrane 180. As the tension on membrane 180 is increased, membrane 180 urges tissue surrounding the longitudinal side of the incision outwardly, thereby retracting the tissue and enlarging proximal access opening 122. At the same time, the expansion of access assembly 100, e.g., to the expanded condition, helps retain access assembly 100 in position within the incision.

Turning now to FIG. 2, once proximal member 120 has been moved to the desired position, e.g., the expanded condition, a surgical procedure may be performed through thoracic access assembly 100 by inserting surgical instrumentation (not shown) and/or withdrawing tissue specimens from the thoracic cavity "T." More particularly, surgical instrumentation (not shown) is inserted through proximal access opening 122 of proximal member 120, through longitudinal passageway 158 defined by membrane 180, through distal access opening 162, and into the thoracic cavity "T" or other internal worksite. As can be appreciated, instrumentation (not shown) and/or specimens of tissue are removed from the thoracic cavity "T" via access assembly 100 in reverse fashion.

Once the procedure has been completed, all instrumentation is removed from the thoracic cavity "T," access assembly 100 is returned to the contracted condition, and distal member 160 is removed from the incision in tissue. Thereafter, the incision may be closed off, e.g., sutured closed.

It will be understood that various modifications may be made to the embodiments disclosed herein. For example, either of the upper frame or lower body member may also be formed of a transparent material. Additionally, while disclosed as being generally rectangular, the frames and body members disclosed herein may include other shapes. Therefore, the above description should not be construed as limiting, but merely as exemplifications of particular embodiments. Those skilled in the art will envision other modifications within the scope and spirit of the claims appended hereto.

What is claimed is:

1. A surgical access assembly for accessing a cavity of a patient, comprising:
   a proximal frame member configured for positioning adjacent an external surface of tissue, the proximal frame member defining a proximal opening therethrough, the proximal frame member including an upper component and a lower component, each of the upper and lower components including a first U-shaped member and a second U-shaped member;
   a distal frame member configured for positioning adjacent an internal surface of tissue, the distal frame member defining a distal opening therethrough; and
   a membrane extending between the proximal frame member and the distal frame member, the membrane having a distal end coupled to the distal frame member and a proximal end disposed between the upper and lower components of the proximal frame member,
   wherein the first U-shaped members of the upper and lower components of the proximal frame member are engaged to one another in snap-fit relation fixedly securing a first section of the membrane therebetween,
   wherein the second U-shaped members of the upper and lower components of the proximal frame member are engaged to one another in snap-fit relation fixedly securing a second section of the membrane therebetween, and
   wherein the first U-shaped members and the second U-shaped members are selectively repositionable relative to one another between a contracted condition, wherein the proximal opening defines a first length, and an expanded condition, wherein the proximal opening defines a second length greater than the first length.

2. The surgical access assembly according to claim 1, wherein one of the first U-shaped members defines a first protrusion and wherein the other of the first U-shaped members defines a first aperture, the first protrusion configured for receipt within the first aperture to engage the first U-shaped members to one another in snap-fit relation; and
   wherein one of the second U-shaped members defines a second protrusion and wherein the other of the second U-shaped members defines a second aperture, the second protrusion configured for receipt within the second aperture to engage the second U-shaped members to one another in snap-fit relation.

3. The surgical access assembly according to claim 2, wherein a portion of the first section of the membrane is disposed between the first protrusion and the first aperture such that, upon snap-fit engagement of the first protrusion within the first aperture, the first section of the membrane is secured between the first U-shaped members of the upper and lower components of the proximal frame member, and
   wherein a portion of the second section of the membrane is disposed between the second protrusion and the second aperture such that, upon snap-fit engagement of the second protrusion within the second aperture, the second section of the membrane is secured between the second U-shaped members of the upper and lower components of the proximal frame member.

4. The surgical access assembly according to claim 2, wherein one of the first U-shaped members defines a plurality of first protrusions and wherein the other of the first U-shaped members defines a plurality of first apertures, the first protrusions configured for receipt within the first apertures to engage the first U-shaped members to one another in snap-fit relation; and
   wherein one of the second U-shaped members defines a plurality of second protrusions and wherein the other of the second U-shaped members defines a plurality of second apertures, the second protrusions configured for receipt within the second apertures to engage the second U-shaped members to one another in snap-fit relation.

5. The surgical access assembly according to claim 1,
wherein the first U-shaped members of the upper and lower components of the proximal frame member are releasably engaged with one another for releasably fixedly securing the first section of the membrane therebetween; and
wherein the second U-shaped members of the upper and lower components of the proximal frame member are releasably engaged with one another for releasably fixedly securing the second section of the membrane therebetween.

6. The surgical access assembly according to claim 1, wherein the membrane defines a first portion of material and a second portion of material, the first portion of material being stiffer than the second portion of material.

7. The surgical access assembly according to claim 6, wherein the first portion of material forms an inner layer of the membrane and wherein the second portion of material forms an outer layer of the membrane.

8. The surgical access assembly according to claim 6, wherein the first portion of material forms an upper portion of the membrane attached to the proximal frame member and wherein the second portion of material forms a lower portion of the membrane attached to the distal frame member, the upper and lower portions of material attached to one another.

* * * * *